US00PP24289P2

(12) United States Plant Patent
Heuger

(10) Patent No.: US PP24,289 P2
(45) Date of Patent: Mar. 4, 2014

(54) ***HELLEBORUS* PLANT NAMED 'COSEH 950'**

(50) Latin Name: ***Helleborus niger*×*Helleborus atrorubens***
Varietal Denomination: COSEH 950

(76) Inventor: Josef Heuger, Glandorf (DE)

( * ) Notice: Subject to any disclaimer, the term of this patent is extended or adjusted under 35 U.S.C. 154(b) by 69 days.

(21) Appl. No.: 13/506,698

(22) Filed: May 10, 2012

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Susan McCormick Ewoldt
(74) *Attorney, Agent, or Firm* — C. A. Whealy

(57) ABSTRACT

A new and distinct cultivar of *Helleborus* plant named 'COSEH 950', characterized by its upright and uniformly mounded plant habit; uniform and freely flowering habit; dark green-colored leaves; long flowering period; single light greyed purple to light yellow green-colored flowers with dark greyed purple-colored margins; and good garden performance.

2 Drawing Sheets

Botanical designation: *Helleborus niger*×*Helleborus atrorubens*.

Cultivar denomination: 'COSEH 950'.

BACKGROUND OF THE INVENTION

The present invention relates to a new and distinct cultivar of *Helleborus* plant, botanically known as *Helleborus niger*× *Helleborus atrorubens*, and hereinafter referred to by the name 'COSEH 950'.

The new *Helleborus* plant is a product of a planned breeding program in Glandorf, Germany. The objective of the breeding program was to create new uniform *Helleborus* plants with unique and attractive plant habit, leaf and flower coloration and resistance to pests.

The new *Helleborus* plant originated from a cross-pollination conducted by the Inventor in Glandorf, Germany in December, 2005 of an unnamed proprietary seedling selection of *Helleborus niger*, not patented, as the female, or seed, parent with an unnamed proprietary seedling selection of *Helleborus atrorubens*, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in January, 2008.

Asexual reproduction of the new *Helleborus* plant by divisions in a controlled greenhouse environment in Glandorf, Germany since March, 2008 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 950'. These characteristics in combination distinguish 'COSEH 950' as a new and distinct *Helleborus* plant:

1. Upright and uniformly mounded plant habit.
2. Uniform and freely flowering habit.
3. Dark green-colored leaves.
4. Long flowering period.
5. Single light greyed purple to light yellow green-colored flowers with dark greyed purple-colored margins.
6. Good garden performance.

Compared to plants of the parent selections, plants of the new *Helleborus* are more uniformly mounded and are more freely flowering.

Plants of the new *Helleborus* can be compared to plants of *Helleborus niger*×*Helleborus atrorubens* 'COSEH 710', disclosed in U.S. Plant Pat. No. 21,063. In side-by-side comparisons conducted in Glandorf, Germany, plants of the new *Helleborus* differed from plants of 'COSEH 710' in leaf and flower color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'COSEH 950' grown in a container.

The photograph on the second sheet is a close-up view of a typical flower of 'COSEH 950'.

DETAILED BOTANICAL DESCRIPTION

The aforementioned photographs and following observations, measurements and values describe plants grown during the winter in 17-cm containers in a glass-covered greenhouse in Glandorf, Germany and under environmental conditions and cultural practices which closely approximate commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus niger*×*Helleborus atrorubens* 'COSEH 950'.

Parentage:

*Female, or seed, parent*.—Unnamed proprietary seedling selection of *Helleborus niger*, not patented.

*Male, or pollen, parent*.—Unnamed proprietary seedling selection of *Helleborus atrorubens*, not patented.

Propagation:

*Type*.—By tissue culture.

*Time to initiate roots, winter*.—About two months at 12° C.

*Time to produce a rooted young plant, winter*.—About six months at 4° C. to 15° C.

*Root description*.—Thick to thin, fleshy; white to brown in color.

*Rooting habit*.—Sparse.

Plant description:

*Plant form and growth habit*.—Herbaceous perennial; upright and uniformly mounding plant habit with flowers held just above the foliar plane; plant shape is globular; moderately vigorous growth habit.

*Plant height*.—About 27.5 cm.

*Plant diameter* (*area of spread*).—About 33.6 cm.

Foliage description:

*Arrangement*.—Leaves arranged in a basal rosette; leaves palmately compound with about seven leaflets per leaf.

*Leaf length*.—About 15.4 cm.

*Leaf width*.—About 22 cm.

*Leaflet length*.—About 10.1 cm.

*Leaflet width*.—About 4.2 cm.

*Leaf shape*.—Palmate; orbicular in outline.

*Leaflet shape*.—Elliptic to ovate and obovate.

*Leaflet apex*.—Broadly acute.

*Leaflet base*.—Cuneate.

*Leaflet margin*.—Sharply serrate; slightly undulate.

*Leaflet texture, upper and lower surfaces*.—Smooth, glabrous; leathery.

*Leaflet venation pattern*.—Pinnate.

*Leaflet color*.—Developing leaves, upper surface: Close to 137B. Developing leaves, lower surface: Close to 138A. Fully developed leaves, upper surface: Between N137C and 147A; venation, close to 144A to 144B. Fully developed leaves, lower surface: Close to 147B; venation, close to 144B.

*Petiole*.—Length: About 5.8 cm. Diameter: About 6 mm. Texture, upper and lower surfaces: Smooth, glabrous. Color, upper and lower surfaces: Close to 138A.

Flower description:

*Flower shape and habit*.—Single rotate flowers arranged in terminal and axillary cymes; freely and uniform flowering habit with about 24 flowers and flower buds developing per plant; flowers facing outwardly to nodding.

*Fragrance*.—None detected.

*Natural flowering season*.—Plants begin flowering about ten months after planting; long flowering period, plants flower from late winter to early spring in Germany.

*Flower longevity on the plant*.—About ten days; flowers not persistent.

*Flower buds*.—Length: About 2 cm. Diameter: About 1.2 cm. Shape: Ovate. Color: Close to 145B; upper surface heavily tinged with close to 182B.

*Inflorescence height*.—About 8.9 cm.

*Inflorescence diameter*.—About 10.4 cm.

*Flower diameter*.—About 5.3 cm.

*Flower depth* (*height*).—About 2.3 cm.

*Petals*.—Transformed into nectaries.

*Sepals*.—Quantity and arrangement: Five arranged in a single whorl. Length: About 3.3 cm. Width: About 2.4 cm. Shape: Elliptic to ovate. Apex: Bluntly broad acute to rounded. Base: Cuneate. Margin: Entire. Texture, upper and lower surfaces: Smooth, glabrous. Color: When opening, upper surface: Close to 145B; margins tinged with close to 187D. When opening, lower surface: Close to 145B tinged with close to 182C; margins tinged with close to 187D. Fully opened, upper and lower surfaces: Close to 186C; center and base, close to 145B to 145C; margins, close to 187D. With development, color becoming closer to 147B to 147C; lower surface tinged with close to 197A.

*Peduncles*.—Strength: Moderately strong. Length: About 17.5 cm. Diameter: About 5 mm. Aspect: About 30° from vertical. Texture: Smooth, glabrous. Color: Close to 144B moderately dotted with close to 181A to 181B.

*Pedicels*.—Strength: Moderately strong. Length: About 2.6 cm. Diameter: About 2 mm. Aspect: Erect to about 25° from the peduncle axis. Texture: Smooth, glabrous. Color: Close to 144B to 144C slightly dotted with close to 181B.

*Reproductive organs*.—Stamens: Quantity per flower: About 75. Filament length: About 1.4 cm. Filament color: Close to 155C. Anther shape: Reniform. Anther length: About 1.5 mm. Anther color: Close to 150D. Pollen amount: Scarce. Pollen color: Close to 4D. Pistils: Quantity per flower: About eight. Pistil length: About 1 cm. Stigma shape: Club-shaped. Stigma color: Close to 150D. Style length: About 9 mm. Style color: Close to 145C. Ovary color: Close to 145B. Nectaries (transformed petals): Quantity per flower: About nine. Length: About 7 mm. Diameter: About 2.5 mm. Shape: Narrow triangular, flattened tubular. Color: Close to 145B; towards the apex, close to 151C.

*Seeds and fruits*.—Seed and fruit development have not been observed on plants of the new *Helleborus*.

Garden performance: Plants of the new *Helleborus* have been observed to have good garden performance and to tolerate rain and wind; plants of the new *Helleborus* have been observed to tolerate high temperatures of about 35° C. and are hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'COSEH 950' as illustrated and described.

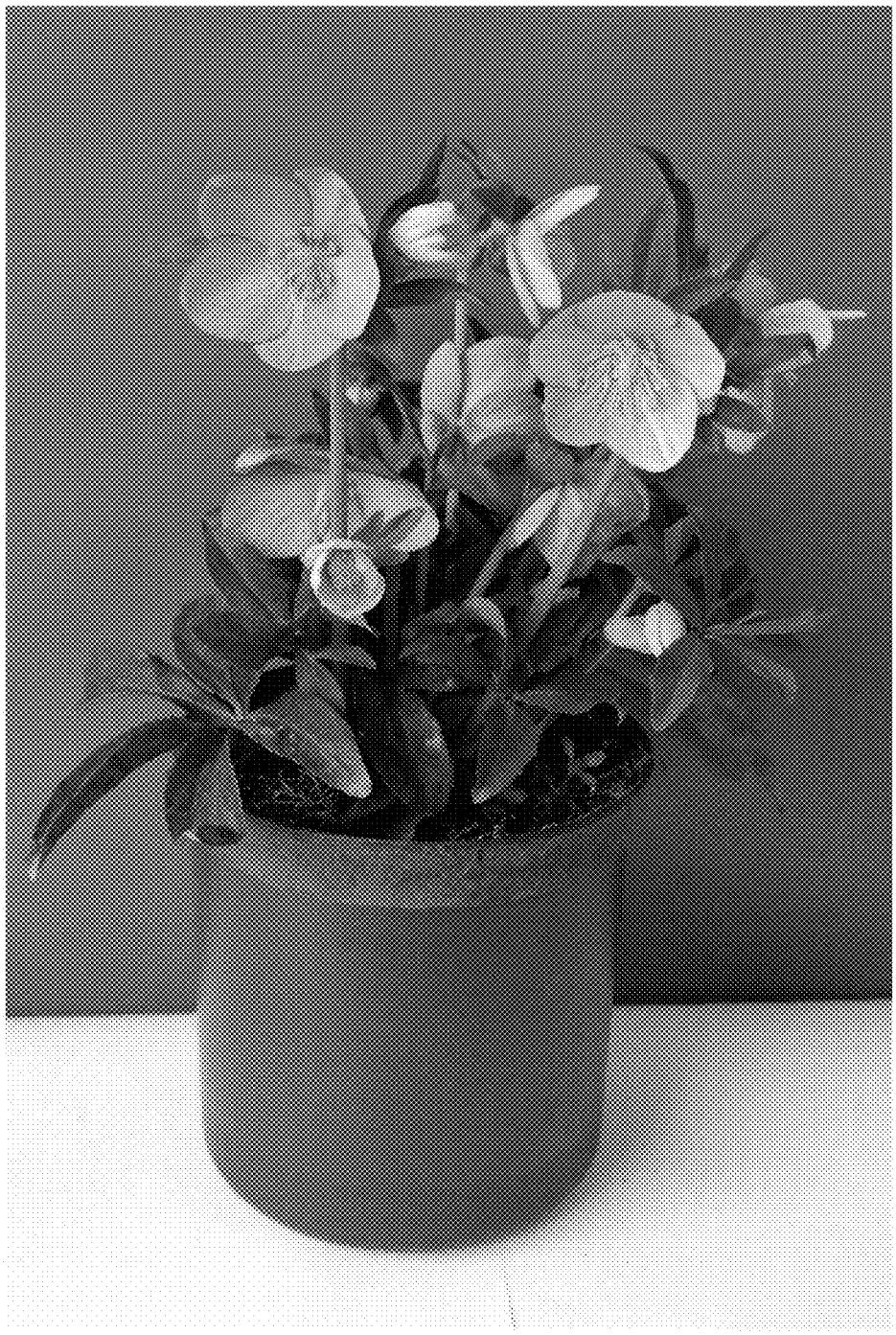

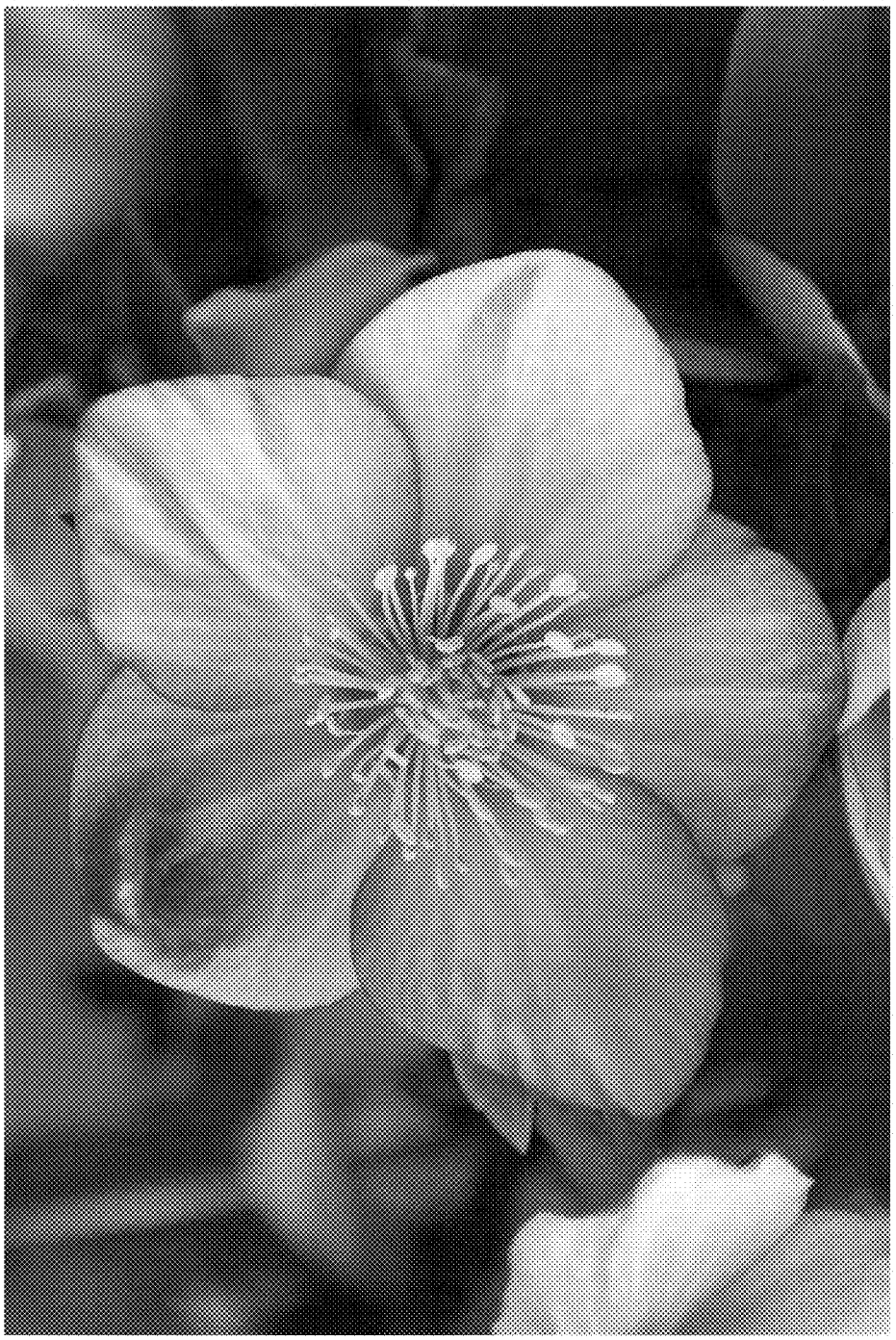

* * * * *